(12) United States Patent
Russo et al.

(10) Patent No.: US 9,349,904 B2
(45) Date of Patent: May 24, 2016

(54) PHOTODETECTOR WITH INTEGRATED MICROFLUIDIC CHANNEL AND MANUFACTURING PROCESS THEREOF

(71) Applicant: STMicroelectronics S.r.l., Agrate Brianza (IT)

(72) Inventors: Alfio Russo, Biancavilla (IT); Giuseppina Valvo, Camporotondo Etneo (IT)

(73) Assignee: STMicroelectronics S.r.l., Agrate Brianza (IL)

( * ) Notice: Subject to any disclaimer, the term of this patent is extended or adjusted under 35 U.S.C. 154(b) by 228 days.

(21) Appl. No.: 13/925,577

(22) Filed: Jun. 24, 2013

(65) Prior Publication Data

US 2014/0021330 A1 Jan. 23, 2014

(30) Foreign Application Priority Data

Jul. 18, 2012 (IT) .............................. TO2012A0634

(51) Int. Cl.
| | |
|---|---|
| *G01N 21/05* | (2006.01) |
| *H01L 31/18* | (2006.01) |
| *G01N 21/64* | (2006.01) |
| *H01L 31/107* | (2006.01) |
| *B01L 3/00* | (2006.01) |

(52) U.S. Cl.
CPC ............ *H01L 31/18* (2013.01); *G01N 21/6454* (2013.01); *H01L 31/107* (2013.01); *B01L 3/5027* (2013.01); *G01N 21/05* (2013.01)

(58) Field of Classification Search
CPC ... G01N 21/53–21/536; G01N 21/85–21/8592
USPC ................................. 250/573–576; 73/53.01
See application file for complete search history.

(56) References Cited

U.S. PATENT DOCUMENTS

| | | | |
|---|---|---|---|
| 8,637,242 B2 * | 1/2014 | Shen et al. ..................... 435/6.1 |
| 2003/0034740 A1 * | 2/2003 | Coll et al. ................. 315/111.21 |
| 2007/0031961 A1 * | 2/2007 | Ho et al. .................... 435/287.2 |
| 2009/0184384 A1 | 7/2009 | Sanfilippo et al. |

OTHER PUBLICATIONS

Chabinyc, M. L. et al., "An Integrated Fluorescence Detection System in Poly(dimethylsiloxane) for Microfluidic Applications," Anal. Chem., vol. 73, pp. 4491-4498, 2001.
Nakazato, H. et al., "Micro fluorescent analysis system integrating GaN-light-emitting-diode on a silicon platform," Lab Chip, vol. 12, p. 3419-3425, 2012.
Shin, K-S. et al., "Characterization of an Integrated Fluorescence-Detection Hybrid Device With Photodiode and Organic Light-Emitting Diode," IEEE Electron Device Letters 27(9):746-748, Sep. 2006.
Lucio Renna et al., "Diagnostic Device with Integrated Photodetector, and Diagnostic System Including the Same," U.S. Appl. No. 13/902,468, filed May 24, 2013, 45 pgs.

* cited by examiner

*Primary Examiner* — Renee D Chavez
(74) *Attorney, Agent, or Firm* — Seed IP Law Group PLLC

(57) ABSTRACT

A photodetector including: a photodiode having a body made of semiconductor material delimited by a first surface, the body forming a first electrode region; a dielectric region, set on top of the first surface and delimited by a second surface; at least one channel extending within the dielectric region, starting from the second surface; and a first metallization, which is set on top of the second surface and is in electrical contact with the first electrode region.

23 Claims, 11 Drawing Sheets

PHOTODETECTOR WITH INTEGRATED MICROFLUIDIC CHANNEL AND MANUFACTURING PROCESS THEREOF

BACKGROUND

1. Technical Field

The present disclosure relates to a photodetector with integrated microfluidic channel and to the manufacturing process thereof.

2. Description of the Related Art

As is known, today there are available numerous diagnostic devices, which find use, for example, in the biological field. In addition, in the field of diagnostic devices, it is known to use photodetectors of an integrated type, each of which includes at least one microfluidic channel optically coupled to a photodiode.

By way of example, the Italian patent application No. TO2012A000501 filed on Jun. 8, 2012in the name of the present applicant (corresponding to U.S. Patent Application No. 13/902,468) describes a photodetector comprising a photodiode, which is formed by a body of semiconductor material and an integrated optical structure, which is arranged on top of the semiconductor body. In addition, the photodetector comprises a microfluidic channel arranged on top of the integrated optical structure. The microfluidic channel houses at least one detection region and is designed to receive a first radiation having a first wavelength. The detection region includes at least one receptor, which is able to bind to a corresponding target molecule, in the case where the latter is present within the microfluidic channel. In turn, the target molecule can bind to a corresponding marker, which, when excited by the first radiation, emits a second radiation having a second wavelength, this second radiation being detectable by the photodiode.

In practice, the patent application No. TO2012A000501 describes a so-called "fluorescence diagnostic device", which is characterized precisely by the use of markers that, when excited with a light radiation at a certain wavelength $\lambda_e$, emit a light radiation of their own at a wavelength $\lambda_f$ greater than the wavelength $\lambda_e$. Consequently, by detecting with the photodiode the light radiation at the wavelength $\lambda_f$, it is possible to derive information on the chemico-physical characteristics of the specimen to be analyzed, which is made to flow within the microfluidic channel. In fact, the light intensity detected by the photodiode is a function of the amount of activated markers, this amount being a function of the number of target molecules.

In particular, the patent application No. TO2012A000501 describes the use of a Geiger-mode avalanche photodiode (GM-APD), also known as "single-photon avalanche diode" (SPAD), in so far as it is able to detect individual photons.

In general, a SPAD is formed by an avalanche photodiode and hence comprises a junction, typically of a P+/N type, or else N+/P type. The junction has a breakdown voltage $V_B$ and is biased, in use, with a reverse-biasing voltage $V_A$ higher in modulus than the breakdown voltage $V_B$, typically higher by 10-20%. In this way, generation of a single electron-hole pair, following upon absorption of an photon impinging upon the SPAD, is sufficient for triggering an ionization process that causes an avalanche multiplication of the charge carriers, with gains in the region of $10^6$ and consequent generation in short times (hundreds of picoseconds) of the avalanche current. The avalanche current can be collected, typically by means of an external circuitry connected to the junction and including anode and cathode contacts and forms an electrical signal at output from the SPAD.

The gain and likelihood of detection of a photon, i.e., the sensitivity of the SPAD, are directly proportional to the value of reverse-biasing voltage $V_A$ applied to the SPAD. However, the fact that the reverse-biasing voltage $V_A$ is appreciably higher than the breakdown voltage $V_B$ causes the process of avalanche ionization, once triggered, to be self-sustaining Consequently, once triggered, the SPAD is no longer able to detect photons, with the consequence that, in the absence of appropriate remedies, the SPAD manages to detect arrival of a first photon, but not arrivals of subsequent photons. In order to be able to detect also these subsequent photons, the avalanche current generated within the SPAD can be quenched, stopping the avalanche ionization process. In practice, one can reduce, for a period of time known as "hold-off time", the effective voltage $V_e$ across the junction, this effective voltage $V_e$ coinciding with the reverse-biasing voltage $V_A$ only in the absence of photons, i.e., in the absence of current in the SPAD. In this way, the ionization process is inhibited and the avalanche current is quenched; then, the initial conditions of biasing of the junction are restored so that the SPAD is again able to detect photons. In order to reduce the effective voltage $V_e$ across the junction following upon absorption of a photon, SPADs adopt the so-called quenching circuits, whether of an active type or of a passive type.

Irrespective of the details of implementation of the SPAD and thanks to the use of the latter, the diagnostic device described in the patent application No. TO2012A000501 is characterized by a high sensitivity. However, according to the patent application No. TO2012A000501, the microfluidic channel is formed on top of the passivation region and of the contacts of the photodiode. Moreover, a Bragg grating is present between the microfluidic channel and the photodiode, in order to increase the intensity of the electrical field inside the microfluidic channel. For these reasons, the optical coupling between the microfluidic channel and the photodiode may not be optimal, in particular for certain wavelengths.

BRIEF SUMMARY

The aim of the present disclosure is to provide a photodetector that will enable at least partial solution of the drawbacks of the known art.

According to the disclosure, a photodetector and a manufacturing method are provided as defined, respectively, in claim 1 and claim 13.

BRIEF DESCRIPTION OF THE SEVERAL VIEWS OF THE DRAWINGS

For a better understanding of the disclosure, embodiments thereof are now described, purely by way of non-limiting example and with reference to the attached drawings, wherein.

DETAILED DESCRIPTION

Figure 1:
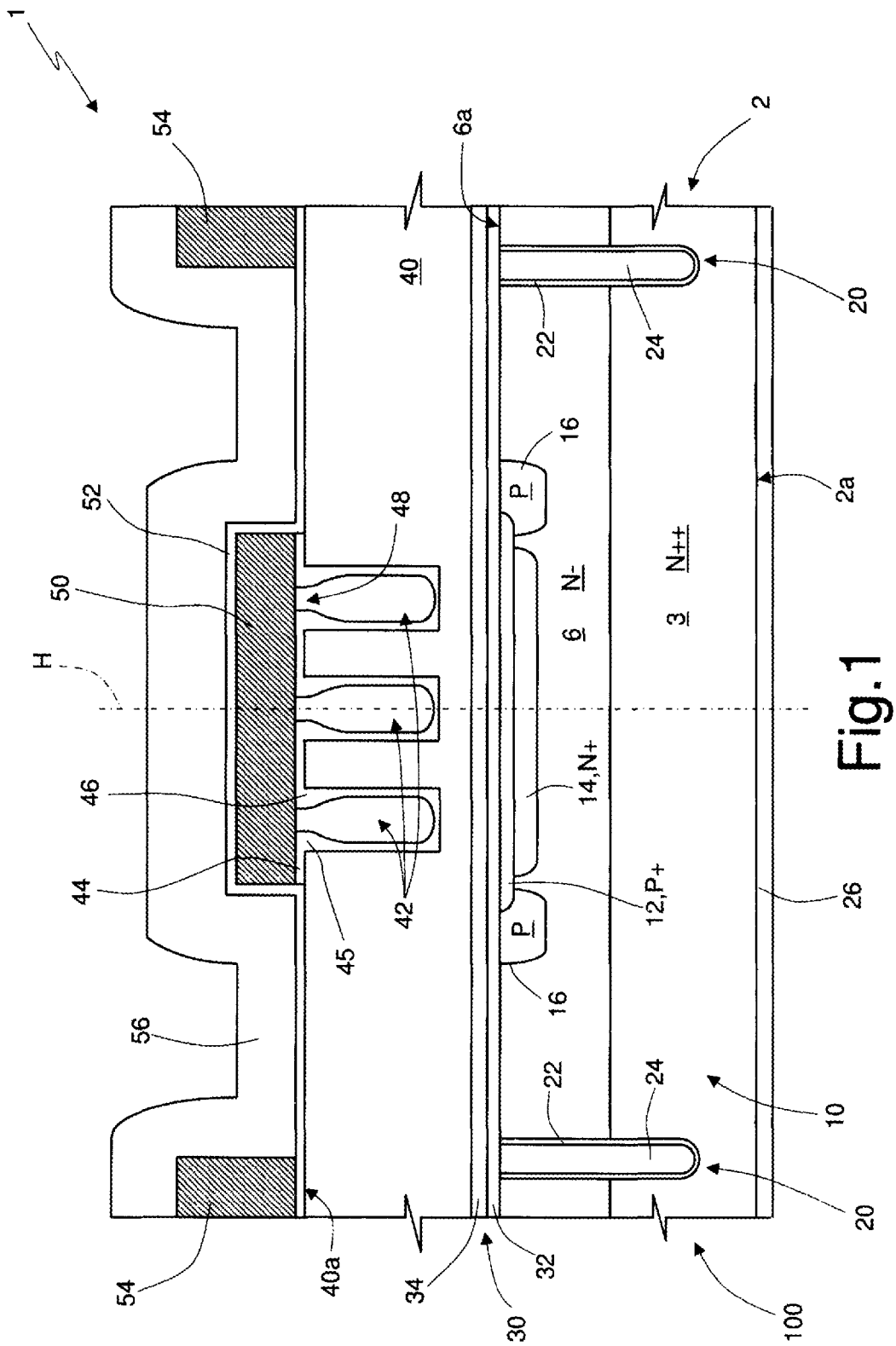
FIGS. 1 and 3 are schematic illustrations of cross sections of embodiments of the present photodetector.

FIG. 1 shows a photodetector 1, which comprises a SPAD 2, which will be referred to hereinafter as "photodiode 2".

In detail, the photodiode 2 is integrated in a die 100, which includes a substrate 3 of semiconductor material, of an N++ type and delimited at the bottom by a bottom surface 2a. Moreover, the photodiode 2 includes an epitaxial layer 6. The epitaxial layer 6 is of an N− type and overlies the substrate 3 in direct contact therewith. Moreover, the epitaxial layer 6 is delimited at the top by an intermediate surface 6a.

The substrate 3 and the epitaxial layer 6 form in practice a body 10 of semiconductor material, which has an axis H that is perpendicular to the intermediate surface 6a and to the bottom surface 2a. Moreover, purely by way of example, the level of doping of the substrate 3 is higher by three orders of magnitude than the level of doping of the epitaxial layer 6.

An anode region 12, of a P+ type, faces the intermediate surface 6a and extends within the epitaxial layer 6. In top plan view, the anode region 12 has, for example, a circular or polygonal shape (for example, rectangular).

An enriched region 14, of an N+ type, extends in the epitaxial layer 6, underneath and in direct contact with, the anode region 12. In top plan view, the enriched region 14 has a circular or polygonal shape (for example, rectangular). The level of doping of the enriched region 14 is higher than the level of doping of the epitaxial layer 6.

For practical purposes, the enriched region 14, the epitaxial layer 6 and the substrate 3 form a cathode region. Consequently, the anode region 12 and the enriched region 14 form a PN junction, which is designed to receive photons and to generate the avalanche current. The enriched region 14 and the epitaxial layer 6 moreover have the purpose of confining a high electrical field in the proximity of the PN junction, reducing the breakdown voltage $V_B$ of the PN junction.

A guard ring 16, of a P type, extends in the epitaxial layer 6; in particular, the guard ring 16 faces the intermediate surface 6a and is arranged on the outside of, and contiguous to, the anode region 12. The guard ring 16 forms a PN diode with the epitaxial layer 6 so as to prevent the so-called "edge breakdown" of the anode region 12.

The photodiode 2 further comprises a lateral-insulation region 20, arranged outside the guard ring 16. The lateral-insulation region 20 extends from the intermediate surface 6a and partially penetrates into the substrate 3.

The lateral-insulation region 20 comprises a channel-stopper region 22, which is arranged more externally, is made of dielectric material (for example, oxide) and is in direct contact with the substrate 3 and with the epitaxial layer 6. Moreover, the lateral-insulation region 20 comprises a metal region 24, which is surrounded by the channel-stopper region 22.

For practical purposes, the lateral-insulation region 20 enables, through the metal region 24, optical insulation of the photodiode 2 from other possible photodiodes formed in the same die 100. In addition, the channel stopper 22 guarantees electrical insulation of the photodiode 2 from these other possible photodiodes. Arranged on top of the intermediate surface 6a is an anti-reflection structure 30, formed by a first anti-reflection layer 32 and by a second anti-reflection layer 34. In particular, the first anti-reflection layer 32 overlies the intermediate surface 6a, whereas the second anti-reflection layer 34 overlies the first anti-reflection layer 32. The first and second anti-reflection layers 32, 34 are formed, respectively, by a first dielectric material and a second dielectric material, which have respective refractive indices $n_1$ and $n_2$. Moreover, the first and second anti-reflection layers 32, 34 have thicknesses $w_1$ and $w_2$, chosen in a such a way that the curve of reflectance as a function of the wavelength has a minimum at $\lambda_e$, where $\lambda_e$ is an excitation wavelength. For example, the first and second dielectric materials may be, respectively, silicon dioxide $SiO_2$ and silicon nitride $Si_3N_4$.

Arranged on top of the integrated optical structure 30 and in particular on top of the second anti-reflection layer 34, is a structural layer 40, formed for example by tetraethyl orthosilicate (TEOS) and delimited at the top by a top surface 40a. Purely by way of example, the structural layer 40 may have a thickness, measured along the axis H, of 2 μm.

Formed within the structural layer 40 is at least one channel 42 designed to enable the flow of a fluid inside it. Purely by way of example, in the embodiment illustrated in FIG. 1 three channels 42 are present.

Each channel 42 extends within the structural layer 40 starting from the top surface 40a, with a depth, measured along the axis H, comprised between 1 μm and 2 μm and with an amplitude, measured along a direction parallel to the top surface 40a, comprised between 0.2 μm and 0.5 μm. Each channel 42 hence has an aspect ratio comprised between 4 and 5.

The side walls and the bottom of each channel 42 are coated with a first coating layer 44, made, for example, of silicon nitride. The first coating layer 44 coats also portions of the top surface 40a arranged between the channels 42.

In greater detail, considering a single channel 42, the first coating layer 44 forms, at top portions of the side walls of the channel 42, a first thickened region 45 and a second thickened region 46, which occlude the top portion of the channel 42 partially, thus forming a top opening 48.

The first and second thickened regions 45, 46 coat in fact the top portions of the side walls of the channel 42, which are adjacent to the top surface 40a, with which they are in direct contact.

In greater detail, except for the thickened regions, the first coating layer 44 has a thickness, for example, of approximately 0.05 μm.

The photodetector 1 further comprises a top region 50, which extends on top of the channels 42, in direct contact with the first coating layer 44; in particular, the top region 50 closes the top openings 48.

In the embodiment illustrated in FIG. 1, the top region 50 is made of metal material, such as for example aluminum, or else an alloy of aluminum and copper.

Extending on top of the top region 50 and in direct contact therewith, is a second coating layer 52, made for example of TEOS. The second coating layer 52 functions as insulating layer and moreover extends on portions of the top surface 40a that surround the top region 50.

The photodiode 2 further comprises a pad 54 of metal material, which functions as anode electrode. The pad 54, which will also be referred to as "anode metallization", is arranged on the top surface 40a and is in ohmic electrical contact with the guard ring 16 and hence with the anode region 12. As illustrated in FIG. 1, the pad 54 is arranged alongside, and at a distance from, the top region 50; moreover, the pad 54 may be partially arranged on top of the second coating layer 52. Purely by way of example, the electrical contact between the pad 54 and the anode region 12 can be obtained by providing conductive connections (not illustrated), which extend through the structural layer 40. For example, the conductive connections could be formed according to known structures, such as with metal strips and/or conductive vias extending through the structural layer.

The photodiode 2 further comprises a cathode electrode 26, which extends underneath the bottom surface 2a of the substrate 3. The anode and cathode electrodes 54, 26 enable biasing of the PN junction with a reverse-biasing voltage $V_A$ higher, in modulus, than the breakdown voltage $V_B$ of the PN junction itself.

The photodetector 2 further comprises a passivation region 56, which extends over the second coating layer 52, with which it is in direct contact. The passivation region 56 partially covers the pad 54 so as to enable electrical connection of the pad 54 to external circuits.

In practice, according to the embodiment illustrated in FIG. 1, the structural layer 40 separates the pad 54 from the active area of the photodiode 2, the latter being formed by the PN junction formed by the anode region 12 and by the enriched region 14. In addition, the second coating layer 52 electrically insulates the top region 50 from the pad 54. The channels 42 are formed underneath the pad 54, i.e., underneath the anode metallization, as well as underneath the passivation region 56 in such a way that they are fully integrated with the photodiode 2.

This being said, each channel 42 is accessible to a specimen of a fluid type to be analyzed. For this purpose, in a way in itself known, the photodetector 1 may comprise, for each channel 42, a first opening and a second opening (not illustrated). In addition, once again in a way in itself known, within one or more of the channels 42 there may be formed at least one detection region 60 (FIG. 2), which may be arranged, for example, on the portion of the first coating layer 44 that coats the bottom of the channel 42.

Figure 2:
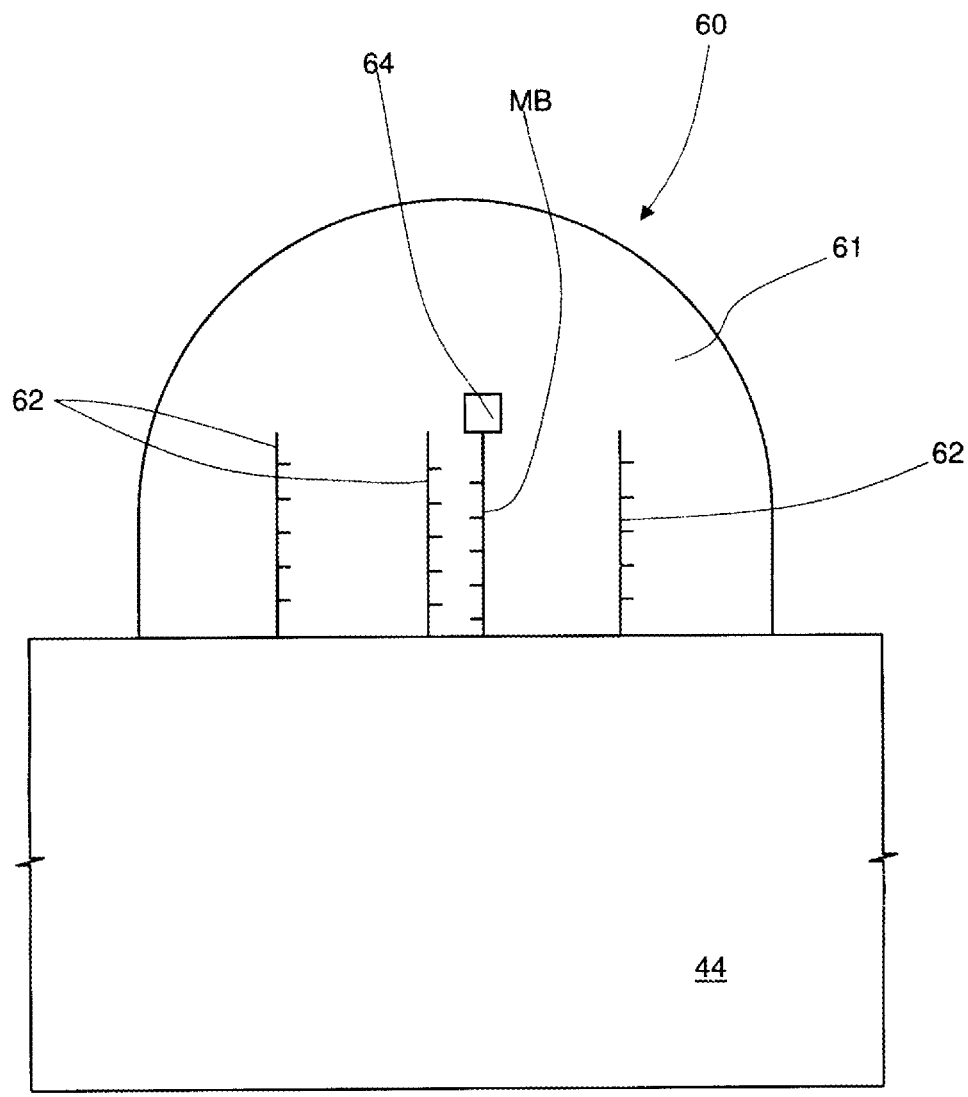
FIG. 2 is a schematic illustration of a cross section of a portion of an embodiment of the present photodetector.

As illustrated purely by way of example in FIG. 2, each detection region 60 is formed, for example, by a drop 61 of biological material, present inside which are receptors 62, which are, for example, immobilized at the first coating layer 44.

By getting the detection regions 60 to come into contact with the specimen to be analyzed, bonds can be set up between the receptors 62 and target molecules MB present in the specimen to be analyzed that flows in the channel 42. It is thus possible to cause activation of markers 64 of a fluorescent (or phosphorescent) type, i.e., binding thereof to the target molecules MB bound to the receptors 62, in such a way that these markers 64 label the receptors 62. For this purpose and purely by way of example, the markers 64 can be originally present in a marking fluid, which is made to flow in the channel 42 after causing flow in the channel 42 of the specimen to be analyzed. In a way in itself known, it is thus possible to illuminate the activated markers with electromagnetic radiation of excitation at the wavelength $\lambda_e$ so that they emit by fluorescence (or phosphorescence) light radiation at a fluorescence wavelength $\lambda_f$, which is detected by the photodiode 2, which in turn generates in response an electrical signal. This electrical signal is indicative of the amount of target molecules MB present in the specimen to be analyzed.

In greater detail, the electromagnetic radiation of excitation can be made to penetrate within the channels 42 in a way in itself known, for example by providing openings. Moreover, since the top region 50 is of metal material, it reflects in the direction of the photodiode 2 the light radiation at the fluorescence wavelength $\lambda_f$ generated within the channels 42. In this embodiment, the electromagnetic radiation of excitation can then propagate within the channels 42 in a guided way.

Figure 3:
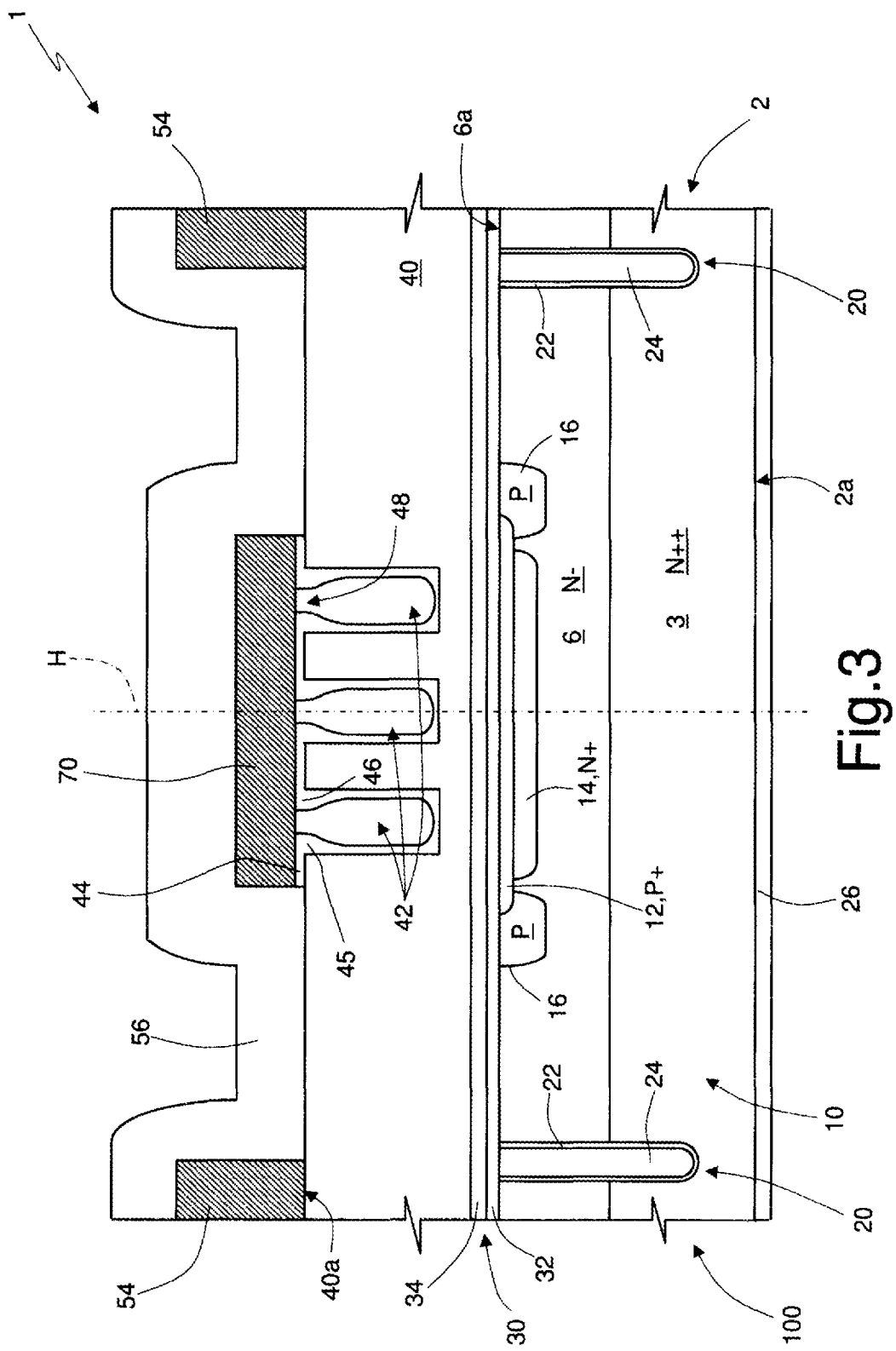

According to a different embodiment, illustrated in FIG. 3, the top region, here designated by 70, is of dielectric material, such as for example TEOS. In this case, the second coating layer 52 is absent and hence the pad 54 is arranged in contact with the top surface 40a.

The embodiment illustrated in FIG. 3 is particularly suited to the case in which the aim is to illuminate the channels 42 using a light source (not illustrated) set on top of the channels themselves and designed to generate electromagnetic radiation of excitation at a wavelength at which the top region 70 is substantially transparent.

Figure 4:
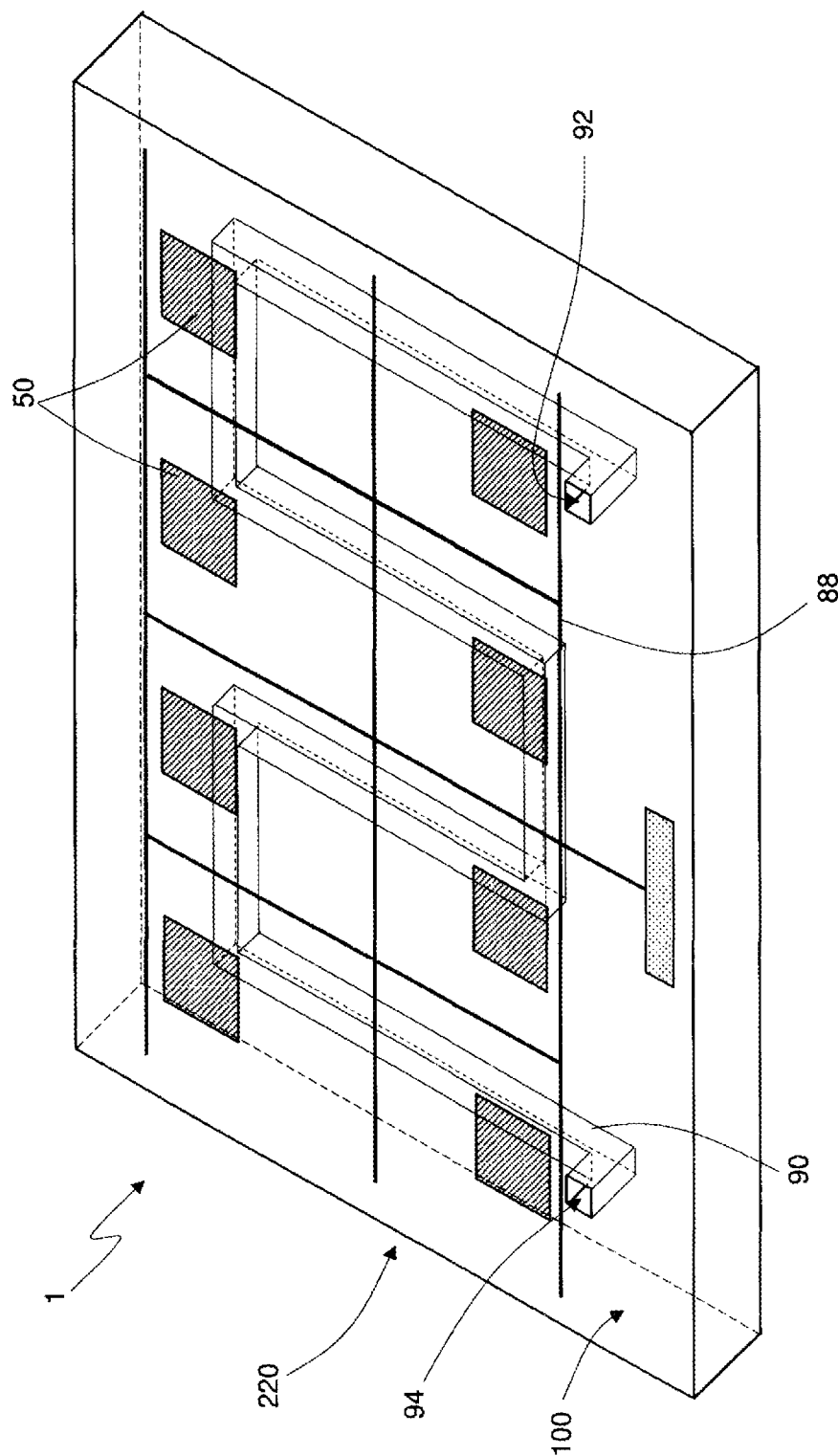
FIG. 4 shows qualitatively a perspective view of portions of one embodiment of the present photodetector.

As illustrated in FIG. 4, the photodiode 2 may belong to an array 220 of photodiodes 2, formed in the die 100. The array 220 may comprise any number of photodiodes, according to the need.

In practice, formed in the die 100 is a two-dimensional array of photodiodes of a SPAD type, grown on one and the same substrate. This two-dimensional array forms a so-called "silicon photomultiplier" (SiPM). The anode metallizations and the cathode electrodes of the SPADs are connected so that they can all be connected to a single voltage generator. In particular, the pads 54 (not illustrated in FIG. 4) are electrically connected to a photomultiplier metallization 88, illustrated schematically in FIG. 4 and having substantially the shape of a grid.

Purely by way of example, FIG. 4 likewise illustrates, once again qualitatively, a channel (designated by 90), which is shared by the photodiodes of the photomultiplier; i.e., it overlies the active areas of these photodiodes. For reasons of clarity, in FIG. 4 the details of the photodiodes are not illustrated, but rather the corresponding top regions 50 are illustrated qualitatively.

In the embodiment illustrated in FIG. 4, the channel 90 has the shape, in top plan view, of a coil. In addition, the channel 90 has an inlet 92 and an outlet 94 to enable entry and exit of the specimen to be analyzed.

The photodiodes 2 of the SiPM can hence be biased at one and the same reverse-biasing voltage $V_A$. In addition, the avalanche currents generated within the photodiodes 2 are multiplexed together so as to generate an output signal of the SiPM equal to the summation of the output signals of the photodiodes 2. The SiPM is hence a device with a large area and high gain that is able to supply, on average, an electrical output signal (current) proportional to the number of photons that impinge upon the SiPM. In fact, each photodiode 2 of the SiPM behaves like an independent binary counter and the output signal of the SiPM is proportional to the number of photodiodes 2 in which the process of avalanche ionization (sensing of a photon) has been triggered, this number being in turn proportional to the number of incident photons.

Figure 5:
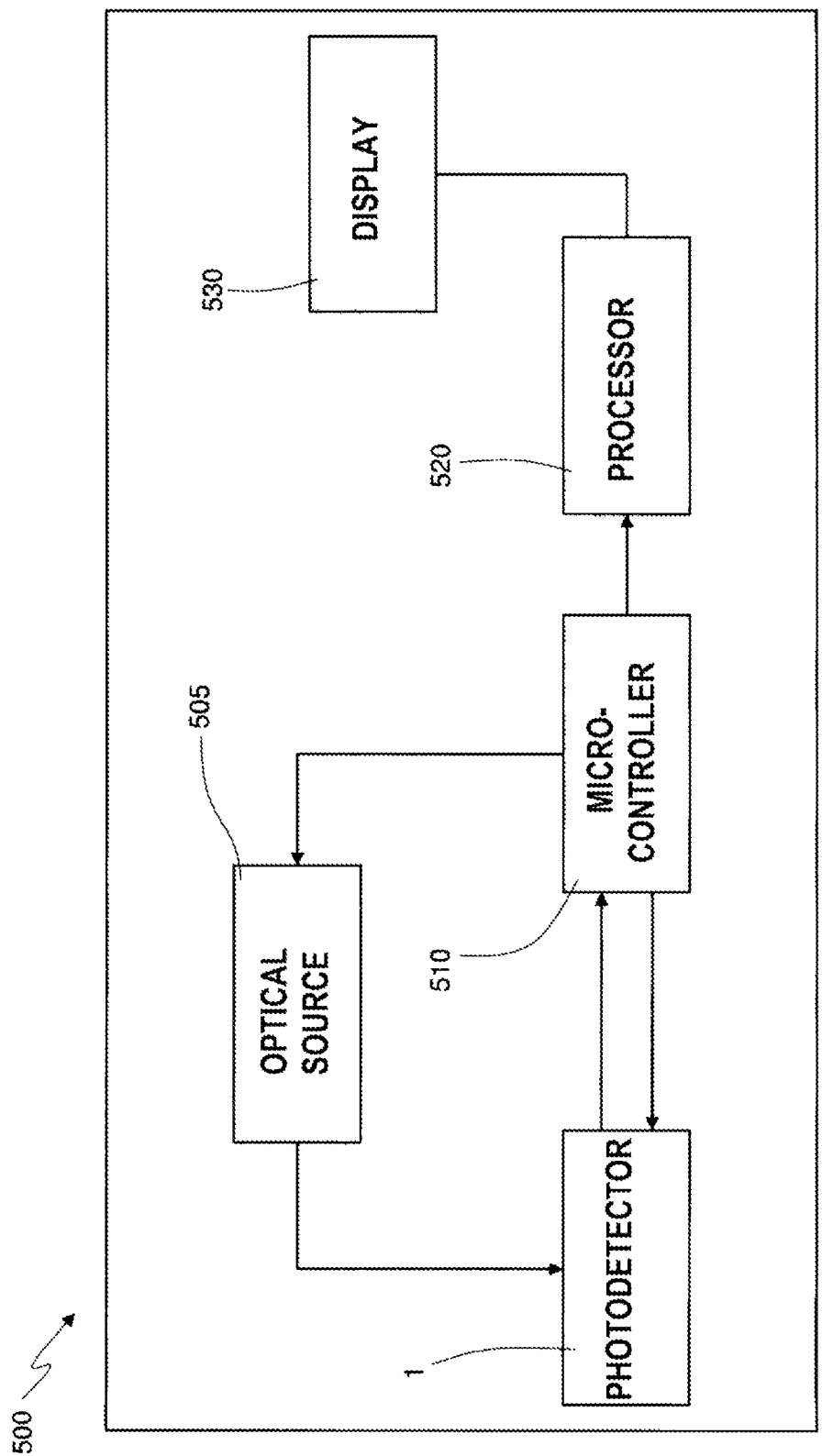
FIG. 5 shows a block diagram of a diagnostic system including the present photodetector.
Figure 6:
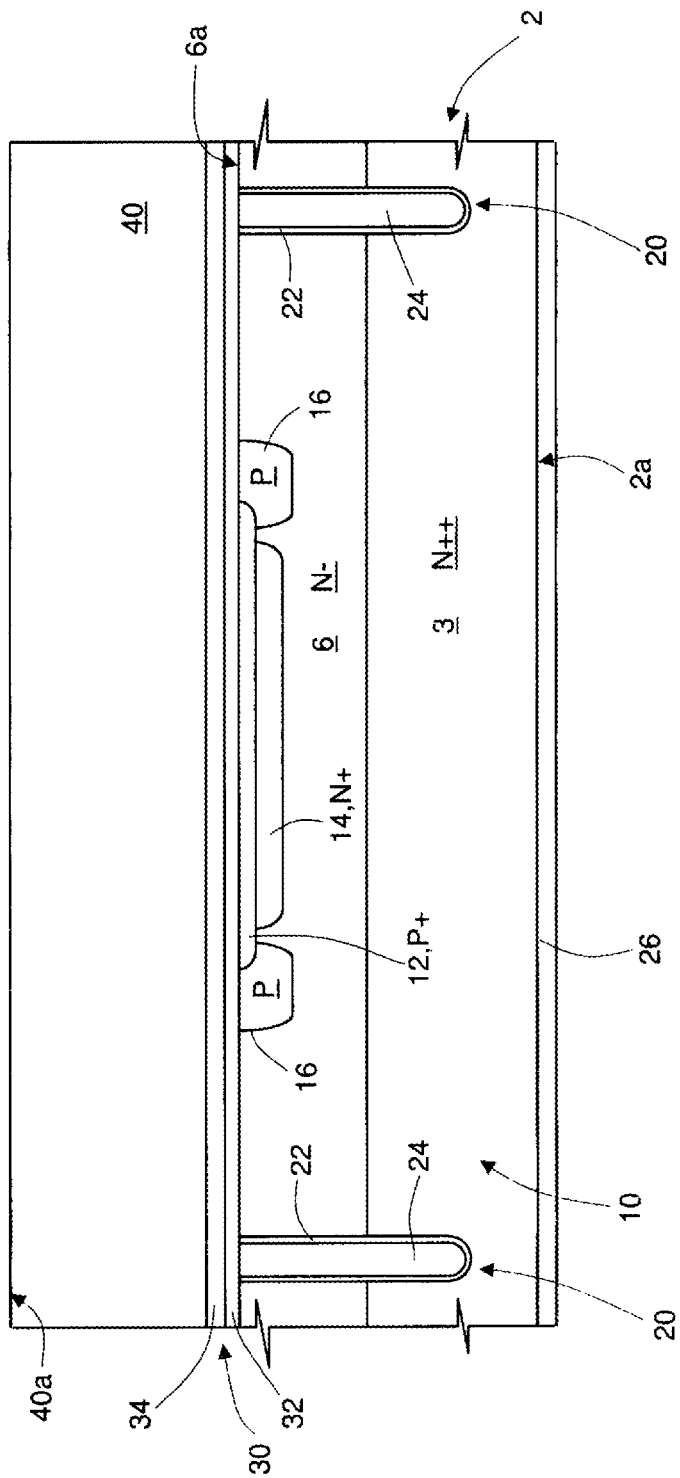
FIGS. 6-11 are schematic illustrations of cross sections of an embodiment of the present photodetector, during successive steps of a manufacturing process.
Figure 7:
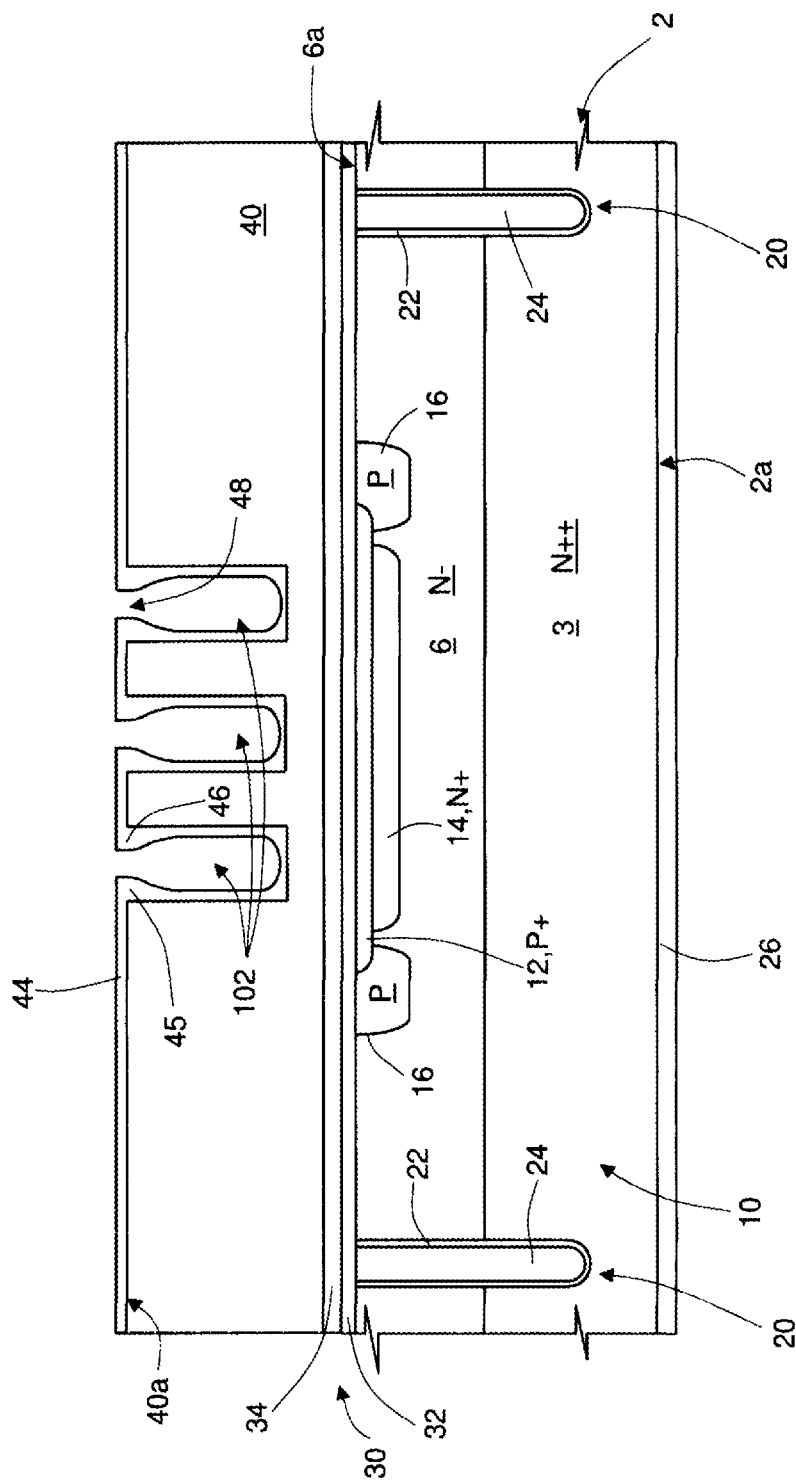
Figure 8:
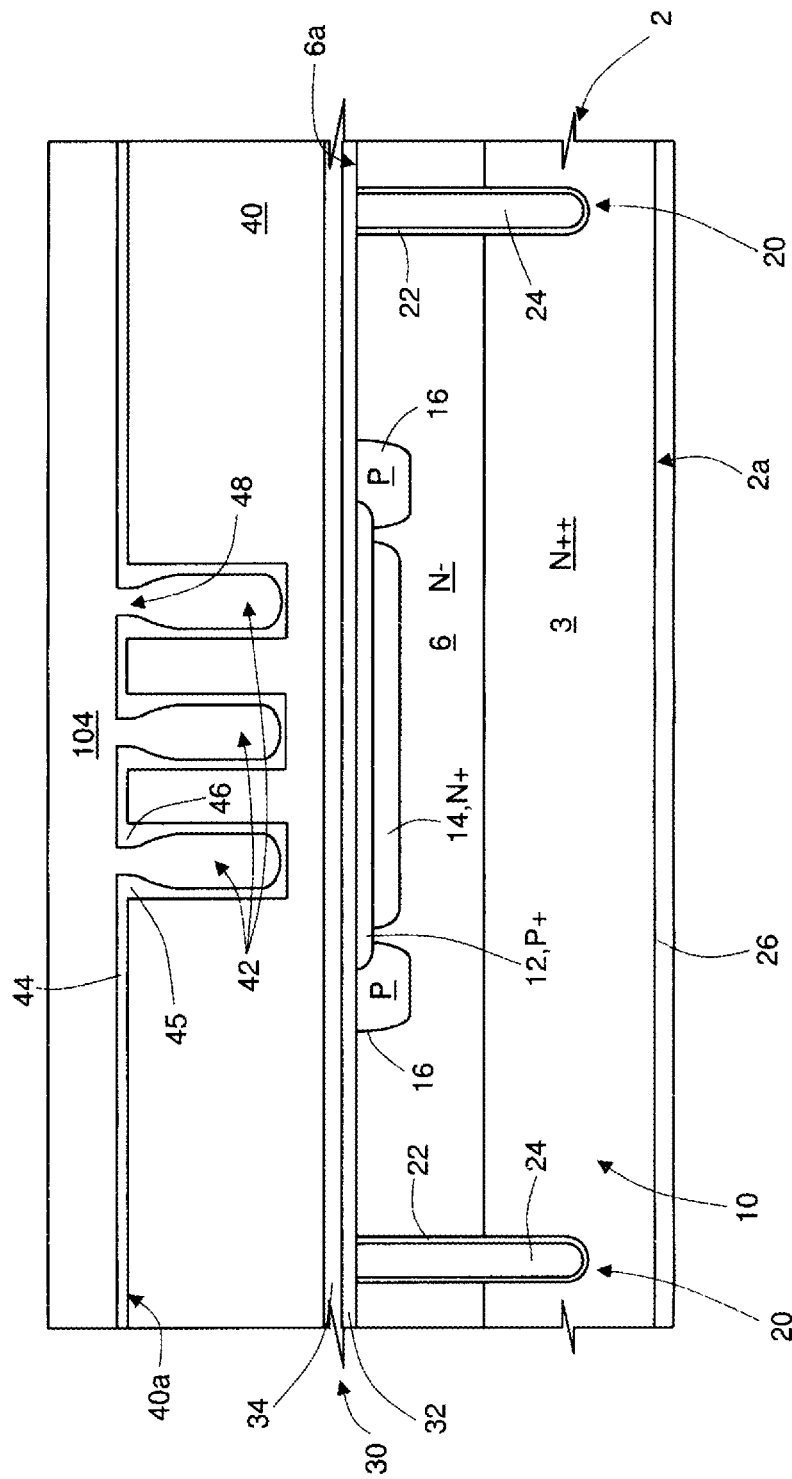
Figure 9:
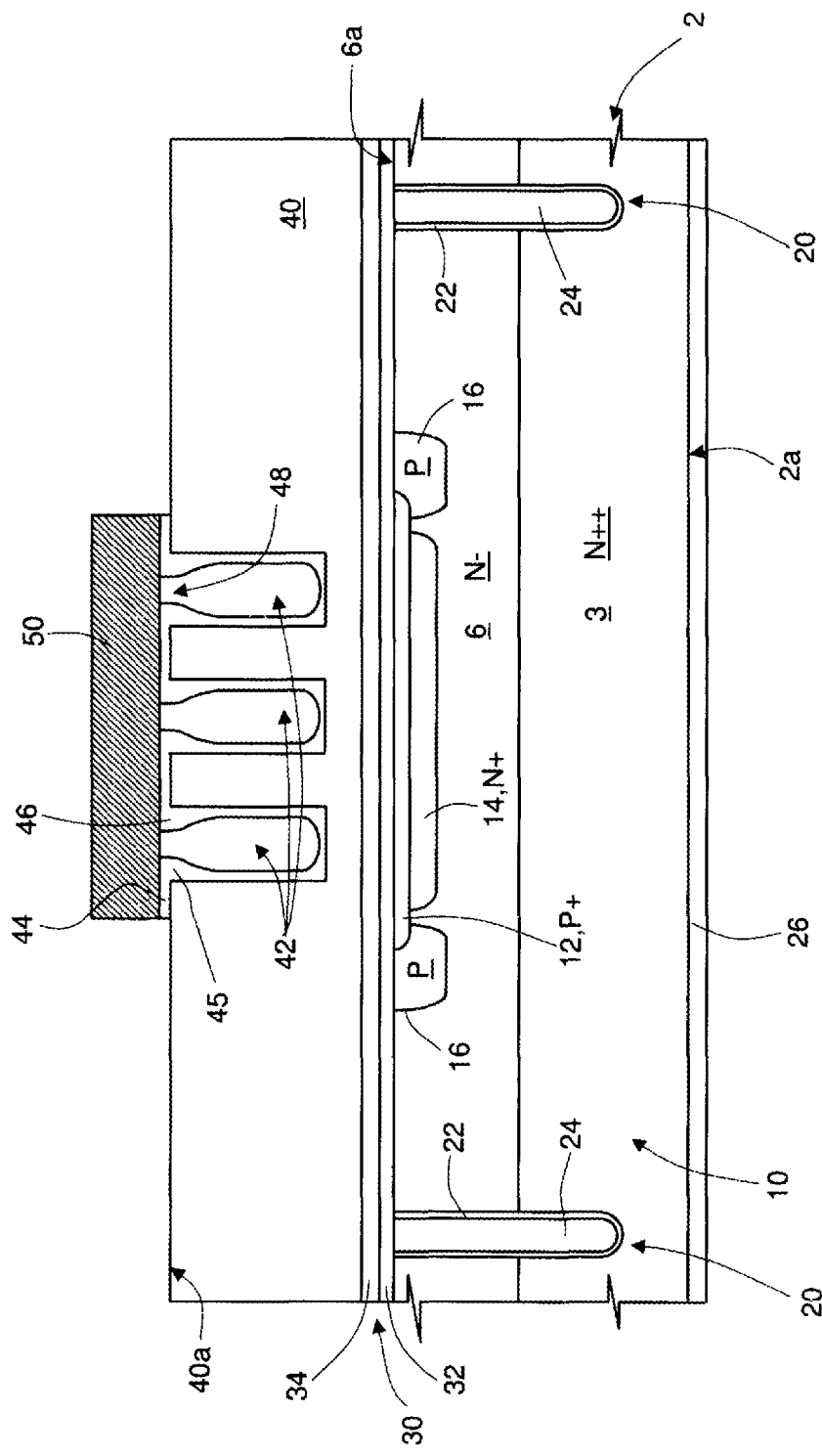
Figure 10:
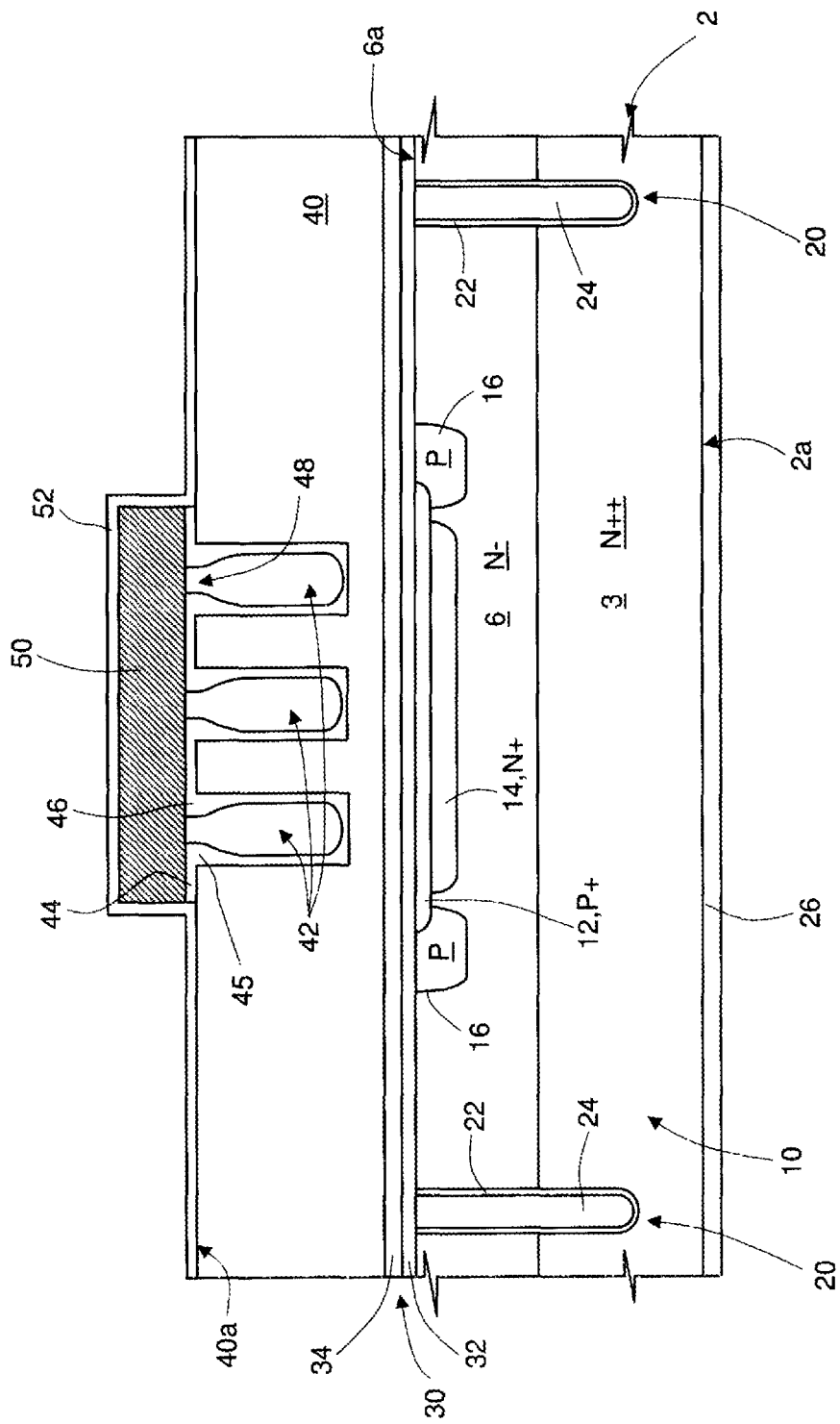
Figure 11:
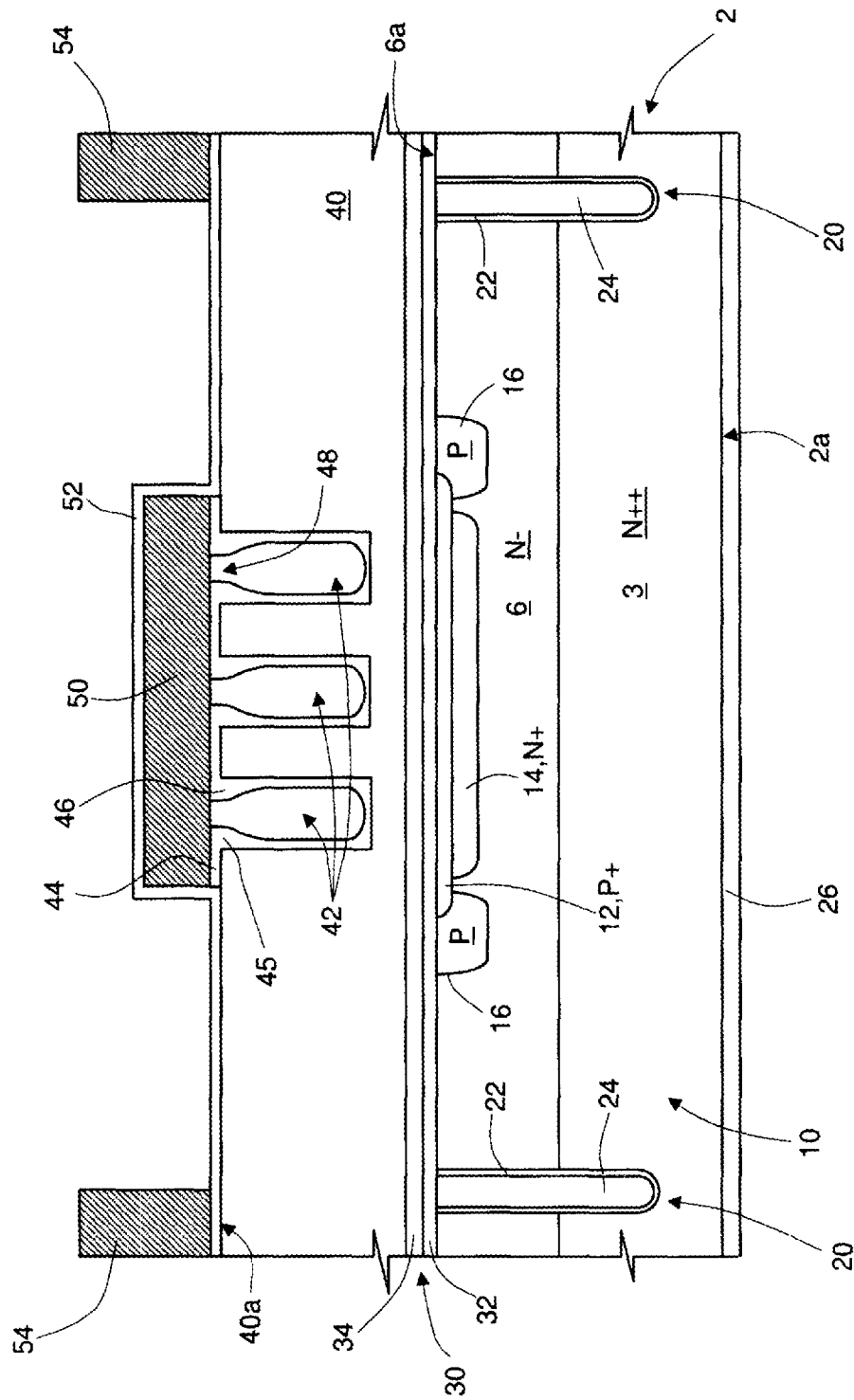

The photodetector 1 can be used in a generic diagnostic system 500 illustrated in FIG. 5, where an optical source 505 illuminates the photodetector 1 and is controlled by a microcontroller unit 510, which is moreover connected to the photodetector 1. The microcontroller unit 510 processes the output signal of the photodetector 1 and supplies a processed signal to a processor 520, which enables analysis of this processed signal and display of the information associated to this processed signal on a display 530.

With reference, purely by way of example, to the embodiment illustrated in FIG. 1, the present photodetector can be obtained by means of the manufacturing process illustrated in FIGS. 6-11.

In detail (FIG. 6), the body 2 of semiconductor material is provided, formed inside which are, in a way in itself known, the anode region 12, the enriched region 14, the guard ring 16, the metal region 24 and the channel-stopper region 22. Moreover formed, in a way in itself known, on top of the body 2 are the first and second anti-reflection layers 32, 34 and the structural layer 40.

Next (FIG. 7), a first photolithographic process is carried out to remove selectively portions of the structural layer 40 so as to form a number of trenches 102 equal to the number of channels 42. The first photolithographic process is performed using a first resist mask. Next, the first coating layer 44 is deposited on the top surface 40a so that it coats the side walls and the bottoms of the trenches 102 and will form the first and second thickened regions 45, 46. At the end of these operations, the trenches 102 are open; in particular, each trench is accessible through the corresponding top opening 48.

Next (FIG. 8), a top layer 104 is formed by means of a first process of sputtering of metal material on top of the first coating layer 44; this first sputtering process is performed at a first temperature, for example comprised between 200° C. and 250° C. The first sputtering process is such that the top layer 104 overlies the first coating layer 44, occluding the top openings 48, without penetrating into the trenches 102; there are thus formed the channels 42, of a closed type. In other words, the top layer 104 is of a so-called non-conformable type since it does not follow faithfully the profile of the layer on top of which it is formed (in the case in point, the first coating layer 44).

Next (FIG. 9), a second photolithographic process is executed using a second resist mask. By means of the second photolithographic process there are selectively removed portions of the top layer 104 arranged laterally with respect to the channels 42, as well as the portions of the first coating layer 44 underlying them. The remaining portion of the top layer 104 thus forms the top region 50.

Next (FIG. 10), the second coating layer 52 is deposited on top of the top region 50 and of the exposed portions of the top surface 40a.

Next (FIG. 11), a second process of sputtering of metal material on top of the second coating layer 52 is carried out in order to form, in a way in itself known, the pad 54. Purely by way of example, this second sputtering process may be carried out at a temperature comprised between 425° C. and 475° C.

In a way not illustrated, there is then formed the passivation region 56. Next, by means of selective removal of portions of the passivation region 56 and of the first and second coating layers 44, 52, the inlets and outlets of the channels 42 are formed, in a way in itself known.

In practice, the operations described with reference to FIGS. 6-10 are carried out after the so-called planarization of the wafer that forms the die 100 and before providing the contacts. In this way, these operations do not entail any degradation of the body 10 of semiconductor material and hence of the photodiode 2.

The advantages that the present photodetector affords emerge clearly from the foregoing discussion.

In particular, the present photodetector is characterized by the integration of one or more channels useful for diagnostic purposes in a SPAD or in a SiPM. In addition, for the reasons described previously, this integration does not entail any increase of the dark noise of the SPAD/SiPM. In fact, unlike what occurs in the known art, the channels are manufactured during the so-called "front-end process", i.e., before providing the metallizations.

Finally, it is evident that modifications and variations may be made to the photodetector and to the manufacturing method described herein, without thereby departing from the scope of the present disclosure.

For example, the types of doping may be reversed with respect to what is described and illustrated herein. Moreover, the mechanisms of binding of the receptors, of the target molecules and of the markers may differ from what has been described. For example, in a way in itself known, the markers may be already present in the specimen to be analyzed, in which case they are already bound to the target molecules, which are then bound to the receptors. In general, in any case, reference to activated markers is made to indicate markers bound to the receptors by binding to the target molecules, irrespective of the details of implementation that have led to the binding.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A photodetector comprising:
   a photodiode that includes:
      a body of semiconductor material having a first surface,
      a first electrode region formed within the body, and
      a photon detection region formed within the body;
   a dielectric region arranged on top of the first surface and having a second surface;
   a channel extending within the dielectric region, starting from said second surface; and
   a first metallization arranged on top of the second surface and electrically coupled with said first electrode region.

2. The photodetector according to claim 1, further comprising a closing region arranged on a top of said channel, said closing region closing said channel at the top of the channel.

3. The photodetector according to claim 2, further comprising a first coating layer of dielectric material, which coats side walls of said channel and forms a first thickened region and a second thickened region that coat portions of the side walls adjacent to the second surface, thereby delimiting a channel opening of the channel.

4. The photodetector according to claim 3, wherein the closing region overlies the first coating layer and is arranged to close said channel opening.

5. The photodetector according to claim 4, wherein the closing region is made of metal material, said photodetector further comprising a second coating layer of dielectric material, arranged on top of the closing region and configured to electrically insulate the closing region from the first metallization.

6. The photodetector according to claim 4, wherein the closing region is made of dielectric material.

7. The photodetector according to claim 2, further comprising a passivation region arranged on top of the closing region and the first metallization.

8. The photodetector according to claim 1, wherein said photodiode is a Geiger-mode avalanche photodiode.

9. The photodetector according to claim 8, further comprising a second electrode region formed in the body, wherein:
   the first electrode region faces the first surface and has a first type of conductivity;
   the second electrode region has a second type of conductivity and is arranged underneath the first electrode region; and
   the first and second electrode regions form a junction having a breakdown voltage, said junction being configured to be biased at a reverse-biasing voltage higher, in modulus, than the breakdown voltage.

10. The photodetector according to claim 1, including a die, said photodiode being formed within the die, said photodetector further comprising a second photodiode, formed in the die and including a second electrode region, said at least one channel being arranged on top of both the first electrode region and the second electrode region.

11. The photodetector according to claim 10, further comprising:
   a second metallization electrically coupled to said second electrode region; and
   a conductive connection electrically coupling said first and second metallizations to each other.

12. A diagnostic system comprising:
   a light source;
   a processing unit; and
   a photodetector that includes:
      a photodiode that includes:
         a body of semiconductor material having a first surface,
         a first electrode region formed within the body, and
         a photon detection region formed within the body;
      a dielectric region arranged on top of the first surface and having a second surface;
      a channel extending within the dielectric region, starting from said second surface; and
      a first metallization arranged on top of the second surface and electrically coupled with said first electrode region.

13. The diagnostic system according to claim 12, further comprising a first coating layer of dielectric material, which coats side walls of said channel and forms a first thickened region and a second thickened region that coat portions of the side walls adjacent to the second surface, thereby delimiting a channel opening of the channel.

14. The diagnostic system according to claim 13, further comprising:
   a metal closing region that overlies the first coating layer and is arranged to close said channel opening; and
   a second coating layer of dielectric material, arranged on top of the closing region and configured to electrically insulate the closing region from the first metallization.

15. The diagnostic system according to claim 13, further comprising:
   a dielectric closing region that overlies the first coating layer and is arranged to close said channel opening.

16. The diagnostic system according to claim 12, wherein:
   the photodetector includes a second electrode region formed in the body;
   the first electrode region faces the first surface and has a first type of conductivity;
   the second electrode region has a second type of conductivity and is arranged underneath the first electrode region; and
   the first and second electrode regions form a junction having a breakdown voltage, said junction being configured to be biased at a reverse-biasing voltage higher, in modulus, than the breakdown voltage.

17. The diagnostic system according to claim 12, including a die, said photodiode being formed within the die, said photodetector further comprising a second photodiode, formed in the die and including a second electrode region, said at least one channel being arranged on top of both the first electrode region and the second electrode region.

18. The diagnostic system according to claim 17, wherein the photodetector includes:
   a second metallization electrically coupled to said second electrode region; and
   a conductive connection electrically coupling said first and second metallizations to each other.

19. A process for manufacturing a photodetector, comprising:
   forming a body of semiconductor material, having a first surface;
   forming an electrode region in the body;
   forming a photon detection region in the body;
   forming a dielectric region on top of the first surface, said dielectric region having a second surface;
   forming a channel within the dielectric region, starting from said second surface; and
   forming a metallization on top of the second surface and electrically coupled to the electrode region.

20. The process according to claim 19, further comprising forming a closing region on top of said channel, the closing region closing a top of said channel.

21. The process according to claim 20, wherein forming the channel comprises forming a trench in the dielectric region and coating side walls of the trench with a first coating layer of dielectric material, the first coating layer forming a first thickened region and a second thickened region that coat portions of the side walls adjacent to the second surface, thereby delimiting a channel opening of the channel.

22. The process according to claim 21, wherein said forming the closing region comprises carrying out a non-conformable deposition on top of the first coating layer in a manner that causes the closing region to close the channel opening.

23. The process according to claim 22, wherein said closing region is made of metal material, the method further comprising forming a second coating layer of dielectric material on top of the closing region before forming the metallization.

* * * * *